United States Patent [19]

Gamble et al.

[11] Patent Number: 4,687,771

[45] Date of Patent: Aug. 18, 1987

[54] METHOD FOR TREATMENT OF MALE IMPOTENCE

[75] Inventors: Donald E. Gamble; Harry L. Hunter; Gordon R. McKinney, all of Evansville, Ind.

[73] Assignee: Bristol-Myers Company, New York, N.Y.

[21] Appl. No.: 793,821

[22] Filed: Nov. 1, 1985

[51] Int. Cl.$^4$ .............................................. A61K 31/50
[52] U.S. Cl. ..................................................... 514/253
[58] Field of Search ......................................... 514/253

[56] References Cited

U.S. PATENT DOCUMENTS

| | | | |
|---|---|---|---|
| 3,381,009 | 4/1968 | Palazzo et al. | 544/127 |
| 4,131,675 | 12/1978 | Silvestrini | 514/252 |
| 4,154,832 | 5/1979 | Silvestrini | 514/253 |
| 4,162,318 | 7/1979 | Silvestrini | 514/252 |

OTHER PUBLICATIONS

L. M. Martin, *Geriatrics*, (Dec. 1980), pp. 79–83.
H. G. Kudish, *Postgraduate Medicine*, vol. 74, No. 4, (Oct. 1983), pp. 233–240.
The Merck Manual, 14th Edition (1982), p. 1602.
Mitchell and Popkin, *Am. J. Psychiatry*, 139:5 (May 1982), pp. 633–637.
Anon., *The Medical Letter*, 26(658), Mar. 30, 1984, p. 35.
Aronoff, *The Lancet*, Apr. 14, 1984, p. 856.
Lansky, et al., *J. Clin. Psychiatry*, 45-232:233, 1984.
Scher, et al., *Am. J. Psychiatry*, 140:1362–1363, 1983.
Raskin, *Am. J. Psychiatry*, 142:1, 1985, p. 142.

*Primary Examiner*—Allen J. Robinson
*Attorney, Agent, or Firm*—Richard P. Ryan

[57] ABSTRACT

Trazodone and its pharmaceutically acceptable salts are useful in the treatment of male sexual impotence.

5 Claims, No Drawings

METHOD FOR TREATMENT OF MALE IMPOTENCE

FIELD OF THE INVENTION

This invention is concerned with a drug bio-affecting body-treating process which employs the triazolopyridine compound 2-[3-[4-(3-chlorophenyl)-1-piperazinyl]-propyl]-1,2,4-triazolo[4,3-a]pyridin-3(2H)-one or a pharmaceutically acceptable acid addition salt thereof.

BACKGROUND OF THE INVENTION

This invention concerns a novel therapeutic treatment for male sexual impotence by the administration of "trazodone" which is the USAN-approved generic name for 2-[3-[4-(3-chlorophenyl)-1-piperazinyl]-propyl]-1,2,4-triazolo [4,3-a]pyridin-3(2H)-one. Trazodone and related compounds are described in U.S. Pat. No. 3,381,009 as having tranquilizing and hypotensive activity. Trazodone has also been described as having utility in the treatment of individuals suffering from the acute phases of stroke (U.S. Pat. No. 4,154,832) and for use in the treatment of Parkinsonism (U.S. Pat. No. 4,162,318) and in combination with L-DOPA in treating Parkinsonism (U.S. Pat. No. 4,131,675). However, trazodone is best known as a potent and safe antidepressant agent and has been accepted internationally for use in the clinical treatment of depression.

Male impotence is a sexual dysfunction which relates to difficulty in achieving and maintaining penile erection. Currently, male impotence is a broad-ranging problem of social, psychologic, and medical significance. There exists today a diversity of possible causes of impotence as well as suggested methods of treatment. These have been described in a number of available literature reviews on male impotence and on male sexual dysfunctioning in general. While impotence can result from psychogenic or physical causes, a review by L. M. Martin in *Geriatrics*, (December 1980), pages 79-83; emphasizes that organic causes of impotence are more common than has been currently believed. Any condition that impairs the endocrine, vascular, neurologic, or anatomic systems can produce impotence. Among various causes of impotence that are specifically implicated are: diabetes, surgery, vascular disease, hypertension and hardening of arteries, side-effects from drugs, and hormonal imbalance.

Concerning the treatment of impotence, H. G. Kudish in *Postgraduate Medicine*, Vol. 74/4 (October 1983), pages 233-240; lists therapies for impotence as being in two categories: surgical and non-surgical. The surgical category comprises implantation of a penile prosthetic device; revascularization of the penis; and incision or excision of Peyronie's plaques. The non-surgical category comprises sex therapy, endocrine therapy, pharmacologic therapy, and electrostimulation. Non-surgical therapies, when effective, are the treatments of choice. Of these, the favored treatment in most instances would be pharmacologic therapy if it was effective. Unfortunately, the use of pharmacologic agents in treatment of impotence has achieved little success. This is evidenced by the absence of any recognized accepted pharmacologic treatment for use in male impotence, although anecdotal reports of the use of various agents, compositions, and formulations abound. Currently, yohimbine, a drug occasionally prescribed for hypertension, is being studied for possible use in the treatment of impotence. Improvement in erectile function after administration of the α-adrenergic blocking agent phenoxybenzamine has also been reported anecdotally.

While reports of beneficial drug effects on sexual functioning in the male are mainly anecdotal, a considerable literature deals with sexual *dysfunction* associated with drug treatment. In general, these effects are considered to be undesirable side effects from any of many medications including *inter alia*, antihypertensives and antidepressants. While most types of sexual dysfunction associated with drug administration appear to be medically benign and reversible with drug discontinuation, an important exception is priapism, which necessitates prompt urologic consultation and which in many cases may require surgical intervention. While not well understood, priapism, a prolonged painful and *abnormal* erection of the penis, can have numerous possible etiologies in addition to administration of pharmacologic agents. It is felt that priapism may involve a different physiologic mechanism than that for normal penile erection. In the state of priapism the viscosity of the blood engorging the penile tissue increases abnormally (of: The Merck Manual, 14th Edition (1982) page 1602). Although the onset of priapism can in some instances be initiated by sexual stimuli, the prolonged painful abnormal erection persists long after the sexual excitement is gone. One reason for the poor understanding of the underlying causes and mechanisms of development of priapism is the low frequency of occurrence of priapism. Since priapism frequently requires surgical intervention, impotence is a possible consequence.

Although several drugs have been reported in the literature as being associated with priapism (see for example: J. E. Mitchell and M. K. Popkin, "Antipsychotic Drug Therapy and Sexual Dysfunction in Man" in *Am. J. Psychiatry*, 139:5 (May 1982) pages 633-637); none of these drugs is employed in treating penile erectile dysfunction. In fact, the potential permanent impotence which can result from priapism causes any pharmacologic agent which may be causally related to priapism to be contra-indicated for use in males. It is to be recognized that induction of the abnormal penile erection of priapism would *not* be considered as a desirable treatment for male impotence. It should also be understood that known agents associated with priapism are not effective in the induction of useful erectile activity in impotent males.

Also found among the many drugs reported to be associated in cases of priapism is trazodone. Representative of these reports are the following:

(1) Anon., *The Medical Letter*, 20(658), Mar. 30, 1984, page 35.
(2) Aronoff, *The Lancet*, Apr. 14, 1984, page 856.
(3) Lansky, et al., *J. Clin. Psychiatry*, 45:232-233, 1984.
(4) Scher, et al., *Am. J. Psychiatry*, 140:1362-1363, 1983.
(5) Raskin, *ibid.*, 142:1, 1985.

While the incidence of trazodone-associated priapism or undesired abnormal erectile activity is very low, nonetheless, these reports would act to teach away from the use of trazodone in treating male impotence, especially since other agents associated with priapism have not been found to be useful in this regard. As the study of the relationship of trazodone and erectile activity has proceeded, however, it has been discovered that trazodone unexpectedly can produce *useful* erectile activity in male mammals. This surprising finding has led to the instant unobvious invention.

In summary, trazodone and its pharmaceutically acceptable salts have heretofore been reported as having only unwanted abnormal and potentially harmful effects on erectil function of male patients. There exists nothing in the prior art which teaches or suggests that trazodone would be useful in the treatment of impotence in males with compromised penile erection function.

SUMMARY OF THE INVENTION

The process of the present invention is intended for treatment of male impotence. The process essentially involves administration of trazodone, or a pharmaceutically acceptable acid addition salt thereof, to a male mammal in need of such treatment. For use in the instant process oral administration of trazodone hydrochloride from about 50 to 400 mg per day is anticipated as being the preferred dosage regimen. Dosage adjustment is to be made depending on the response seen in each individual.

DETAILED DESCRIPTION OF THE INVENTION

Erectile impotence has been defined by Masters and Johnson (W. H. Masters, V. E. Johnson; *Human Sexual Inadequacy*, Little, Brown and Company, Boston, 1970, page 157) as the "inability to achieve or maintain an erection [of] quality sufficient to accomplish successful coital connection". Since erectile impotence can result from a variety of underlying causes ranging from purely psychogenic to completely physical dysfunctioning, it would be unrealistic to expect a single treatment modality to be effective in all cases. In current medical practice, impotence is treated by determining the underlying cause or causes and then treating them whenever possible. When irreversible organic impotence is found, however, penile prosthesis implantation is considered the most beneficial treatment. For psychogenic causes of impotence, the underlying condition is treated with psychopharmacologic agents and/or behavioral therapies. In a majority of cases, identification of the underlying causes of male impotence is either very complex or cannot be determined with certainty. Currently, refractory cases of organic impotence, resulting from neurologic causes, for example, can be identified by a comprehensive diagnostic approach which includes nocturnal penile tumescence monitoring and laboratory testing.

The technique of nocturnal penile tumescence monitoring makes use of bursts of autonomic central nervous system activity which occur regularly every 90 to 110 minutes during sleep. These periods are characterized by a variety of objective physiologic changes which include rapid eye movement (REM), increased respiration, increased heart rate, and penile erection. When organic impotence is present, nocturnal penile tumescence will fail to occur or be abnormally diminished. If the problem is not due to physical dysfunction, a normal nocturnal penile tumescence pattern will be observed.

A study in monkeys demonstrated that trazodone produced penile tumescence in 40% of the animals tested. The tumescence seen with trazodone developed within 10 minutes and lasted for about 50-60 minutes. Spontaneous detumescence is associated with normal erectile activity as opposed to the abnormal erectile activity of priapism. Following study in monkeys, trazodone was demonstrated to cause significant increase in nocturnal penile tumescence in three of six normal male volunteers. This study on sleep-related erections in normal males was placebo-controlled and compared the effects of trazodone and trimipramine. The increased erectile activity in the study subjects was seen only with trazodone, thus tending to confirm the monkey study which indicates that trazodone may produce or enhance erectile activity in a significant proportion of Anthropoidea and might be useful in treatment of human male impotence.

Analysis of reported episodes of unusual erectile activity for depressed male patients being administered trazodone indicates that in some instances the patient or physician has considered the erectile activity to be beneficial. Several of these clinical cases are summarized in Table 1.

TABLE 1

| Beneficial Erectile Activity With Trazodone | | | | |
|---|---|---|---|---|
| Ex. No. | Pt. File No | Age (Years) | Dosage (mg.) | Remarks |
| 1 | 39-MGE-0128 | 59 | 100-200 | Pt. was semi-impotent prior to therapy with trazodone. |
| 2 | 39-MKE-0097 | 50 | 50-250 | Although erections persist following intercourse, pt. continues with medication, reporting that the "benefit outweighs the effect..." |
| 3 | 39-MLA-0043 | 57 | 150 | Pt. had first erection in 5 years within 2 days of trazodone treatment. No erections since trazodone discontinued. |
| 4 | 39-MHD-0006 | 44 | unknown | Pt. had a fibrotic mass at the base of the penis and was impotent prior to trazodone therapy. |
| 5 | 75-SRUSA-MO385-0284 | 50 | 100 | Pt. had loss of libido for several years. Sexual functioning returned after starting on trazodone. |
| 6 | 87-SRUSA-MO785-0235 | 52 | 75-100 | Pt. had been impotent for last 5 years. Within 3 days of trazodone treatment, pt. experienced a return of sexual function. |
| 7 | 39-MLD-0032 | 44 | 200-400 | MD reports that pt. is happy with his increased erectile activity and wished to remain on trazodone. |

Administration of trazodone according to the present invention may be made by the parenteral, oral, or rectal routes. The oral route is preferred, however. The clinical dosage range for the treatment of male sexual impotence is about the same as for antimdepressant usage, that is, from about 50 mg up to about 400 mg per day. It is recommended that trazodone be given accompanied by some food and starting at the level of 50 mg per day. Preferably, the drug should be taken at bedtime. The drug may then be increased by 50 mg increments, as tolerated, every 3 to 7 days. As the total dosage increases, the drug may be administered in divided doses. No more than 300 mg of trazodone is to be given as a single dose. Male patients being treated with trazodone for impotence should be monitored carefully by their attending physician during the dose-titration period of treatment. Since the dosage should be tailored to the individual patient, the usual practice is to commence with a dose of about 50 mg per day administered at bedtime and then to increase the dose every 3 to 7 days by 50 mg at each dosage time until the desired response is observed or until the patient exhibits side effects. Administration of the daily dosage in divided doses may be recommended in some instances. The emergence of side effects such as dizziness, drowsiness, or prolonged or inappropriate penile erection serves as indication to the attending physician or health specialist that a discontinuation or reduction in the amount of trazodone administered would be appropriate.

What is claimed is:

1. A method for treating male sexual impotence which comprises administering a non-toxic therapeutically effective dose of trazodone or a pharmaceutically acceptable acid addition salt thereof to a patient in need of such treatment.

2. The method of claim 1 wherein trazodone hydrochloride is employed and dosage is by the oral route.

3. The method of claim 2 wherein said patient is an adult and a daily dose of from about 50 mg to 400 mg is employed.

4. The method of claim 3 wherein said daily dose is divided and administered b.i.d.

5. The method of claim 3 wherein said daily dose is divided and administered t.i.d.

* * * * *